United States Patent [19]

Akamatsu et al.

[11] 3,947,471

[45] Mar. 30, 1976

[54] BENZ (c) FLUORAN COMPOUNDS AND RECORDING SHEET CONTAINING THEM

[75] Inventors: Takashi Akamatsu, Ashiya; Koichi Koga, Toyonaka; Mitsuru Kondo, Kawanishi; Makoto Miyake, Nishinomiya; Hiroshi Twasaki, Takatsuki; Masatoshi Matsuo, Ibaragi; Seiji Hotta, Hirakata; Isao Yuji, Takarazuka; Yukiaki Ito, Minoo, all of Japan

[73] Assignees: Sumitomo Chemical Company, Ltd., Osaka; Kanzaki Paper Manufacturing Co., Ltd., Tokyo, both of Japan

[22] Filed: May 20, 1974

[21] Appl. No.: 471,698

Related U.S. Application Data

[63] Continuation of Ser. No. 188,541, Oct. 12, 1971, abandoned.

[30] Foreign Application Priority Data

Dec. 26, 1970 Japan............................... 46-130387
Dec. 26, 1970 Japan............................... 46-130392

[52] U.S. Cl................................ 260/335; 282/27.5
[51] Int. Cl.$^2$......................................... C07D 311/84
[58] Field of Search..................................... 260/335

[56] References Cited

UNITED STATES PATENTS

| | | | |
|---|---|---|---|
| 1,194,380 | 8/1916 | Hagenbach......................... | 260/335 |
| 3,654,314 | 4/1972 | Farber et al....................... | 260/335 |
| 3,669,711 | 6/1972 | Kimura et al....................... | 260/335 |
| 3,691,203 | 9/1972 | Koga et al.......................... | 260/335 |
| 3,849,164 | 11/1974 | Schwab et al...................... | 260/335 |

FOREIGN PATENTS OR APPLICATIONS 2,024,859  11/1970  Germany

Primary Examiner—Norma S. Milestone
Attorney, Agent, or Firm—Stevens, Davis, Miller & Mosher

[57] ABSTRACT

Novel benz[c]fluoran compounds such as 2-phenylamino-8-diethylamino-benz[c]fluoran, 2-(2',4',6'-trimethylphenylamino)-8-diethylamino-benz[c]fluoran and N-[8-diethylaminobenz[c]fluoran-2-yl]-N-[6-diethylaminofluoran-2-yl]amine, which are useful as a coloring material for record material systems such as pressure-sensitive copying paper or heat-sensitive copying paper, wherein colored images formed by an electron-donoracceptor color-forming reaction between coloring material and acidic material.

9 Claims, No Drawings

BENZ (C) FLUORAN COMPOUNDS AND RECORDING SHEET CONTAINING THEM

This is a continuation of application Ser. No. 188,544 filed Oct. 12, 1971, and now abandoned.

This invention relates to a chromogenic compounds for use in recording sheet which develops color images by an electro donor-acceptor color-forming reaction between chromogenic material and acidic material which react upon contact to produce a color.

More particularly, the present invention relates to novel benz[c]fluorans represented by the following general formulas (I), which have never been disclosed in prior art references, methods for the preparation thereof and recording sheet containing the same as chromogenic materials.

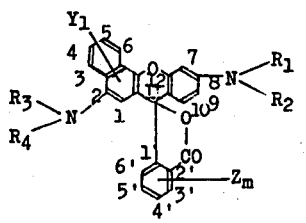

(I)

wherein $R_1$ and $R_2$ each signify hydrogen, a lower alkyl, a lower alkoxyalkyl, a lower haloalkyl, benzyl, or a benzyl substituted by a lower alkoxy, a lower alkyl, a halogen or nitro; $R_3$ signifyies hydrogen, a lower alkyl, a lower alkoxyalkyl, a lower hydroxyalkyl, a lower haloalkyl, a lower cyanoalkyl, carbamoyl, a lower alkenyl, a lower alkynyl or a group of

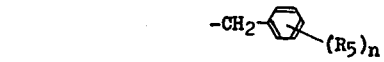

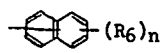, 

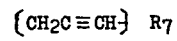, 

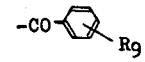, 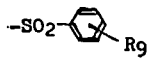

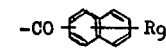, 

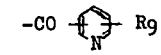, 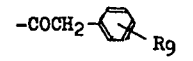

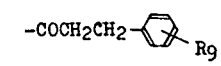, 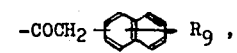

or    $-CH_2COOR_{10}$ (wherein $R_5$ stands for hydrogen atom, a lower alkyl, a lower acyl, a lower haloalkyl, a lower alkoxy, nitro, a halogen, a lower alkoxycarbonyl, a lower alkanesulfonyl, benzenesulfonyl, toluenesulfonyl, a halobenzenesulfonyl or methoxybenzenesulfonyl; $R_6$ represents hydrogen, a lower alkyl, a lower alkoxy, a halogen, nitro, amino, or an amino group substituted by at least one lower alkyl group; n is an integer of 1 to 7; $R_7$ stands for hydrogen, a lower alkyl, a lower haloalkyl, phenyl, a halophenyl, tolyl, methoxyphenyl or nitrophenyl; $R_8$ represents hydrogen, a lower alkyl, a lower alkenyl, a lower alkynyl, a lower haloalkyl or a lower alkoxyalkyl; $R_9$ represents hydrogen, a lower alkyl, a lower alkoxy, a halogen or nitro; $R_{10}$ stands for hydrogen, a lower alkyl, benzyl or phenyl; $Y_1$ signifies hydrogen, a lower alkyl, a lower alkoxy, a halogen, nitro, amino or an amino substituted by at least one lower alkyl group; Z is hydrogen, a lower alkyl, a halogen, a lower alkoxy, nitro, amino, an amino substituted by at least one lower alkyl group or a group of $$-N = CH - B$$

wherein B represents hydrogen, a lower alkyl, phenyl unsubstituted or substituted by a lower alkyl, a lower alkoxy, a halogen or nitro; m is an integer of 1 to 4; and $R_4$ signifies a group of

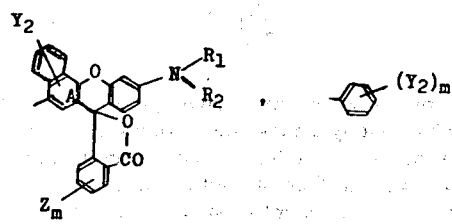

or 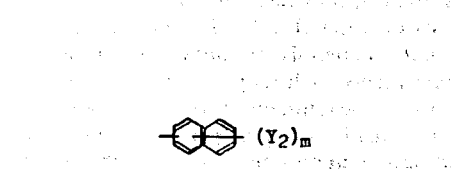

wherein $R_1$, $R_2$ and m are as defined above, and $Y_2$ signifies hydrogen, a lower alkyl, a lower alkoxy, a halogen, nitro, amino or an amino substituted by at least one lower alkyl group, and A signifies benzene or naphthalene nucleus.

Throughout the present specification, the term "lower" as is seen in "lower alkyl group" indicates that the number of carbon atoms is 1 to 4.

In the present specification, the present benz[c]-fluorans are named and the position substituted in the benz[c]fluoran nucleus are numbered as follows:

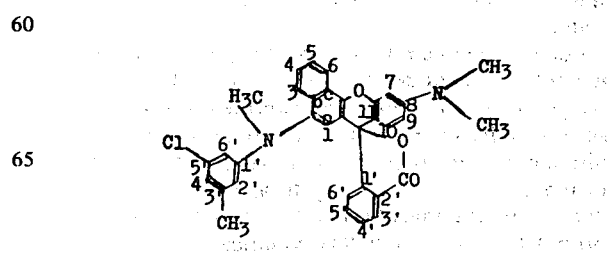

2-(N-methyl-3'-methyl-5'-chloro-anilino)-8-dimethylamino-benz[c]fluoran

So far oil carbon paper was used for making out documents and slips as office work materials. It has drawbacks that it is liable to stain clothes and hands and it is troublesome to insert the oil carbon paper between documents and slips.

In order to eliminate the inefficiencies and defects of the oil carbon paper, pressure-sensitive copying paper or noncarbon paper, which is economic and handy, has recently made its debut in place of the oil carbon paper complying with demand for speed-up of office works.

Heretofore, leucoauramines, leucomethyleneblues, phthalides and fluorans are well known as color precursors. They are colorless or nearly colorless compounds, which may change to a certain coloring matter when they are brought into contact with acidic electron-acceptor as explained below.

For example, 2-methyl-6-diethylamino-fluoran having the following formula (II) is one of the well-known color precursors which are colorless compounds under ordinary condition but change to red coloring matters by opening their lactone ring when they are brought into contact with acidic electron-acceptor.

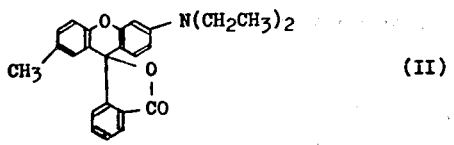

(II)

The pressure-sensitive copying paper is usually prepared by coating a back side of one sheet of paper with a color precursor such as a leucoauramine or a fluoran, and coating a surface of another sheet of paper with an acidic electron-acceptor such as kaolin, bentonite, activated clay, acid clay, aluminum silicate, attapulgite, metal oxides, metal chlorides, metal sulfates, organic acids such as phenols, aliphatic acids or tannic acid, or phenolic resins such as p-phenylphenol-formaldehyde resin, p-cyclohexylphenol-formaldehyde resin, etc. The pressure-sensitive copying paper is used by placing the coated papers upon one another so that the back side of the first paper may be faced to the surface of the second paper, and the back side of the second paper to the surface of the third paper and so on. By applying pressure or impact to the papers by means of a pencil, a ball-point pen or a typewriter on the first paper, the material on the back side and the electron-acceptor substances on the surface of the papers are brought into contact with each other, whereby the colorless pressure-sensitive material moves to the electron-acceptor layer and undergoes color development and therefore colored images can be obtained.

The compound (II) has defects that, when used as color precursor for pressure-sensitive copying paper, it stains capsules in undesired red color because it is slightly soluble in water or slightly acidic or alkaline water.

Further, it has a relatively high vapor pressure so that it tends to vaporize from the capsules to form ghost images which contaminate regular images on the pressure-sensitive copying paper and to cause the images to disappear on the paper during storage for a long period of time.

The present invention has technical advance over prior arts in the following points:

1. These fluoran compounds represented by the general formula (I) are colorless and stable in air at ordinary temperature, but the compounds (I) change in color from white to red, blue, green or black when they are brought into contact with an acidic electron-acceptor explained in detail above.

2. These fluoran compounds (I) show all sorts of dark colors, for example, deep red, dark green, dark blue-green, dark greenish black, or black according to the number, kind and position of substituents.

These various colors are due to the same benz-[c]fluoran nucleus except the kind, number and position of substituents. The present benz[c]fluoran compounds have almost the same color developing speed and the pressure-sensitive copying paper obtained by mixing the present benz[c]fluoran compounds shows no lag of the color developing time and changes the color of the image.

It is also possible to use the said compounds together with other color precursors such as C.V.L. (crystal violet lactone), B.L.M.B. (benzoyl leucomethyleneblue) or 2-methyl-6-diethylaminofluoran, etc. to obtain a special color such as blue-black or black image on the paper without spoiling the other color precursers. These are significant features of the present invention.

3. These benz[c]fluoran compounds are well soluble under colorless condition in a non-volatile non-polar solvent used for preparing a recording sheet. Examples of the non-polar solvent are as follows:

Chlorinated benzenes such as trichlorobenzenes and tetrachlorobenzenes; chlorinated biphenyls such as dichlorodiphenyls, trichlorodiphenyls, and tetrachlorodiphenyls; alkylated benzenes; alkylated naphthalenes such as dimethylnaphthalene and dipropylnaphthalene; mineral oil; paraffin oil; olive oil; and tricresyl phosphate, etc.

Such good solubility in the above solvents is probably caused by the naphthalene ring in the benz-[c]fluoran nucleus represented by the general formula (I). Good solubility particularly in the aromatic solvents makes it easy to prepare the recording sheet and to obtain a deep image on the paper.

4. The present fluoran compounds have no solubility and good stability in water, acids or alkalis. For example, 2-(2',4'-dimethylphenylamino)-8-diethylaminobenz[c]fluoran can be boiled with an alkali solution without being destroyed.

5. The present benz[c]fluoran compounds have good fastness to light, moisture and sublimation.

The obtained deep image on this recording sheet does not disappear or change in color by moisture or droplets of water, or by exposure to sun-light or by heating.

The recording sheet prepared with use of the present benz[c]fluoran compound endures storage for a long period of time without the disappearance of the image on the documents and slips.

6. The present fluoran compounds have high color-developing speed. Such color formation occurs just at once when the fluoran compounds in the form of crystals or a solution in the above-cited solvents are brought into contact with the acidic electron-acceptor. Then, the recording sheet prepared with use of the present benz[c]fluoran compounds gives vivid deep images on the paper at the moment when a pressure or impact is applied onto the paper by means of a pencil, a ball-point pen or a typewriter.

7. The images on the recording sheet prepared with a mixture of the present benz[c]fluoran compounds do not change in color owing to the same color-developing speeds caused by the same benz[c]fluoran nucleus. The present benz[c]fluoran compounds represented by the general formula (I) may be prepared by the following three methods.

In the presence of a dehydrating agent, benz[c]fluoran (I) can be prepared by reacting a o-(2'-hydroxy-4'-aminobenzoyl)-benzoic acid represented by the formula,

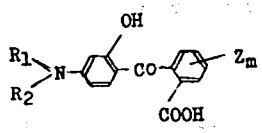

wherein $R_1$, $R_2$, Z and m are as defined above, with a compound represented by the formulas,

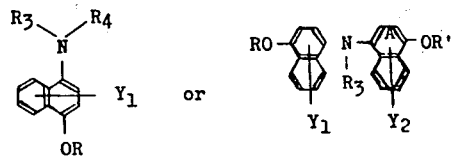

wherein $R_3$, $R_4$, $Y_1$, $Y_2$ and A are as defined above and R and R' represent hydrogen atom or a lower alkyl group, to obtain a 11-(o-carboxyphenyl)-2,8-diamino-benz[c]-xanthohydrol represented by the formulas,

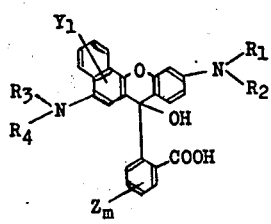

or

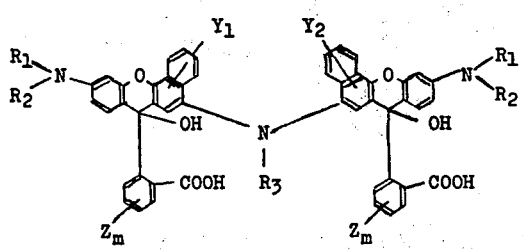

wherein $R_1$, $R_2$, $R_3$, $R_4$, $Y_1$, $Y_2$, A, Z and m are as defined above, and by ring-closing the resultant.

The reaction may be effected at a temperature of 0° to 300°C for several hours or sometimes for a few days in the presence of a dehydrating-condensing agent. Examples of the dehydrating-condensing agent include sulfuric acid; phosphorous pentoxide; phosphoric acid; polyphosphoric acid; anhydrous metal halides such as anhydrous tin chloride or bromide, anhydrous zinc chloride or bromide, anhydrous aluminum chloride or bromide, anhydrous ferric chloride or bromide; phosphoric pentachloride or bromide; phosphorous trichloride or bromide, and anhydrous hydrogen chloride or fluoride.

If necessary, carbon disulfide, chlorinated benzenes, or nitrobenzenes are used as a solvent for the reaction.

The resulting xanthohydrol is converted to the fluoran compound represented by the formula (I) by closing the ring.

After the reaction is over, the reaction mixture is poured into ice or water to separate solid, and if desired, the mixture is neutralized with a solution of an alkali such as caustic soda, potassium hydroxide and the like thereby to obtain the xanthohydrol.

In order to convert the resulting xanthohydrol to the fluoran compound represented by the formula (I) by closing the ring, the xanthohydrol may be dissolved and heated in a solvent and then the mixture may be cooled or concentrated to obtain the fluoran compound (I) as white crystals.

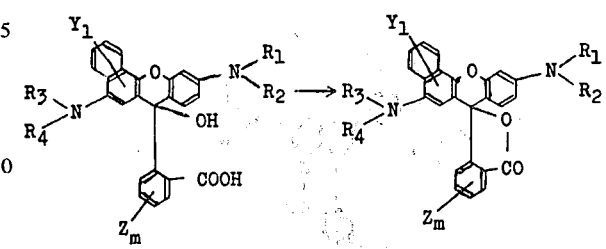

wherein $R_1$, $R_2$, $R_3$, $R_4$, $Y_1$, Z and m are as defined above.

As a solvent for the ring-closure, aromatic hydrocarbon solvents such as benzene, xylene, etc.; nuclear halogenated aromatic hydrocarbon solvents such as chlorobenzene, bromobenzene, dichlorobenzenes, trichlorobenzenes, etc.; alcohols such as methanol, ethanol, etc.; amide solvents such as dimethylformamide, diethylformamide, etc.; sulfoxide solvents such as dimethylsulfoxide, diethylsulfoxide, etc.; aliphatic hydrocarbon solvents such as n-hexane, cyclohexane, etc.; halogenated aliphatic hydrocarbon solvents such as chloroform, bromoform, methylchloroform, etc.; and ethers such as dimethyl ether, diethyl ether, etc. are useful.

The cyclization is often facilitated by the addition of an aliphatic amine such as dimethylamine, trimethylamine, diethylamine, triethylamine, etc.; an aliphatic aminoalcohol such as ethanolamine, propanolamine, etc.; or a heterocyclic base substance such as pyridine, picoline, etc.

White crystals, which separate on heating and cooling in any one of these cyclization solvents or a mixture thereof, are filtered and washed with a nonpolar solvent such as cyclohexane, n-hexane, diethyl ether to obtain a colorless compound (I). In case of a compound having a stable lactone ring, white crystals are often obtained merely by neutralizing a hydrochloric acid or sulfuric acid solution thereof with caustic soda, potassium hydroxide, etc.

The second method is similar to the first method. Thus, a 2-(4'-amino-1'-hydroxy-2'-naphthoyl)-benzoic acid represented by the formula,

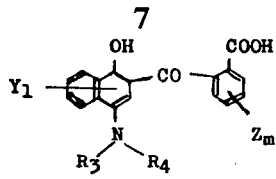

wherein $R_3$, $R_4$, $Y_1$, Z and m are as defined above, may be reacted with a m-aminophenol at a proper reaction temperature in the presence of a dehydrating agent as explained above to obtain a benz[c]fluoran compound represented by the general formula (I).

The reaction proceeds as follows:

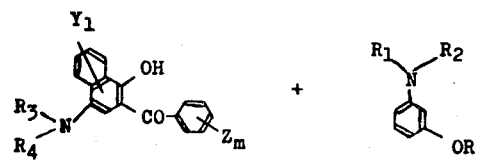

wherein R, $R_1$, $R_2$, $R_3$, $R_4$, $Y_1$, Z and $m$ are as defined above. The purification procedure after the reaction is the same as that in the first method.

The third method is accomplished by the use of a fluoran compound prepared by the first or second methods. Thus, a benz[c]fluoran represented by the formulas,

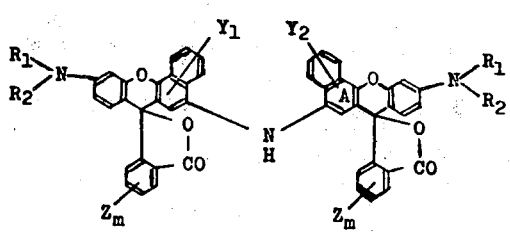

or

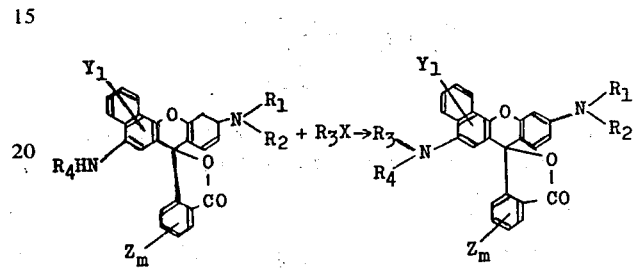

wherein $R_1$, $R_2$, $R_4$, $Y_1$, A, Z and m are as defined above, which has at least one hydrogen atom in the amino substituent at 2-position of the benz[c]fluoran nucleus is treated with an alkylating agent, an acylating agent or a sulfonylating agent as explained below in the presence or absence of a dehydrating agent or a dehydrohalogenating agent. The reaction is properly carried out at 0° – 200°C for several hours or sometimes for a few days, if desired, in the presence of a solvent such as benzene, toluene, xylene, chloroform, 1,2-dichloroethane, ether, dioxane, N,N-dimethylformamide, dimethylsulfoxide, alcohols, etc.

The reaction proceeds as follows:

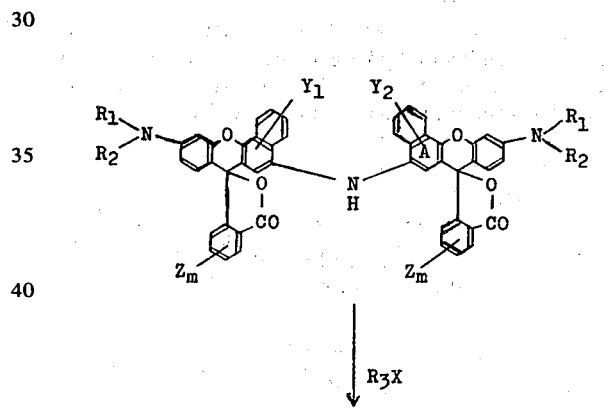

or

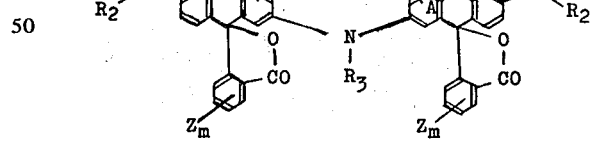

wherein $R_1$, $R_2$, $R_3$, $R_4$, $Y_1$, $Y_2$, Z and m are as defined above and X signifies a residue of the alkylating, acylating or sulfonylating agent such as halogen atom, hydroxy group, $SO_4^{--}$, $PO_3^{---}$, etc.

Examples of the acylating, alkylating and sulfonylating agents which may be used in the above-mentioned reaction include:

1.
Acetic anhydride
Propionic anhydride
Butyric anhydride
Propiolic anhydride

Crotonic anhydride
Benzoic anhydride
m-Chlorobenzoic anhydride
o-Chlorobenzoic anhydride
m-Nitrobenzoic anhydride
p-Bromobenzoic anhydride
o-Bromobenzoic anhydride
m-Methylbenzoic anhydride
p-Methoxybenzoic anhydride
o-Methoxybenzoic anhydride
2.
Acetyl chloride
Propionyl chloride
Acryloyl chloride
Methacryloyl chloride
Crotonoyl chloride
Acetyl bromide
Butyryl bromide
Propiolyl bromide
Crotonyl bromide
Benzoyl chloride
m-Chlorobenzoyl chloride
p-Nitrobenzoyl chloride
o-Nitrobenzoyl chloride
m-Bromobenzoyl chloride
p-Methylbenzoyl chloride
o-Methylbenzoyl chloride
m-Methoxybenzoyl chloride
Benzoyl bromide
p-Chlorobenzoyl bromide
o-Chlorobenzoyl bromide
m-Nitrobenzoyl bromide
p-Bromobenzoyl bromide
o-Bromobenzoyl bromide
m-Methylbenzoyl bromide
p-Methoxybenzoyl bromide
o-Methoxybenzoyl bromide Also, as the alkylating agent, the following compounds are preferable.

3. Esters:
Dimethyl sulfate
Diethyl sulfate
Dipropyl sulfate
Trimethyl phosphate
Triethyl phosphate
Methyl benzenesulfonate
Ethyl benzenesulfonate
Methyl p-toluenesulfonate
Propyl p-toluenesulfonate
Methoxyethyl p-toluenesulfonate
Methyl methanesulfonate
Propyl methanesulfonate
4. Lower alkyl halides:
Methyl chloride
Methyl bromide
Ethyl bromide
Propyl chloride
Butyl chloride
5. Benzyl halides:
Benzyl chloride
m-Nitrobenzyl chloride
p-Chlorobenzyl chloride
o-Chlorobenzyl chloride
m-Bromobenzyl chloride
p-Methylbenzyl chloride
o-Methylbenzyl chloride
m-Methoxybenzyl chloride
Benzyl bromide
p-Nitrobenzyl bromide
o-Nitrobenzyl bromide
m-Chlorobenzyl bromide
p-Bromobenzyl bromide
o-Bromobenzyl bromide
m-Methylbenzyl bromide
p-Methoxybenzyl bromide
o-Methoxybenzyl bromide
6. Allyl halides:
Allyl chloride
2-Methylallyl chloride
2-Ethylallyl chloride
2-Butenyl chloride
Cinnamyl chloride
7. Propargyl halide derivatives:
Propargyl chloride
2-Butynyl chloride
2-Pentynyl chloride
2-Pentynyl bromide
3-Phenyl-2-propynyl bromide
8. Dihalides:
o-Xylylene dichloride
m-Xylylene dichloride
p-Xylylene dichloride
4,5-Dimethyl-o-xylylene dichloride
3,6-Dimethyl-o-xylylene dichloride
4-Methyl-m-xylylene dichloride
2,5-Dimethyl-m-xylylene dichloride
4,6-Dimethyl-m-xylylene dichloride
4-Hydroxy-5-methyl-m-xylylene dichloride
2-Hydroxy-5-methyl-m-xylylene dichloride
4-Bromo-6-methoxy-m-xylylene dichloride
2-Bromo-5-methyl-p-xylylene dichloride
2,5-Dimethoxy-p-xylylene dichloride
4,4'-Bis-chloromethyldiphenyl
3,3'-Dimethyl-4,4'-bis-chlorodiphenyl
4,4'-Bis-chloromethyldiphenylmethane
3,3'-Dimethoxy-4,4'-bis-chloromethyldiphenylmethane
4,4'-Bis-chloromethyldiphenylethane
3,3'-Dimethoxy-4,4'-bis-chloromethyldiphenylethane
4,4'-Bis-chloromethyldiphenylether
3,3'-Dimethyl-4,4'-bis-chloromethyldiphenylether
4,4'-Bis-chloromethylstilbene
3,3'-Dimethyl-4,4'-bis-chloromethylstilbene
3,3'-Dimethoxy-4,4'-bis-chloromethylstilbene
2-Butenylene dichloride
1,4-Dimethyl-2-butenylene dichloride
1-Methyl-2-butenylene dichloride
1-Ethyl-2-butenylene dichloride
2-Butynylene dichloride
1-Methyl-2-butynylene dichloride
o-Xylylene dibromide
m-Xylene dibromide
p-Xylylene dibromide
4,5-Dimethyl-o-xylylene dibromide
4-Methyl-m-xylylene dibromide
2,5-Dimethyl-m-xylylene dibromide
4-Methoxy-m-xylylene dibromide
4-Hydroxy-5-methyl-m-xylylene dibromide
4-Chloro-6-methoxy-m-xylylene dibromide
2,5-Dimethyl-p-xylylene dibromide
2,5-Dimethoxy-p-xylylene dibromide
2-Bromo-5-methyl-p-xylylene dibromide
4,4'-Bis-bromomethyldiphenyl
3,3'-Dimethyl-4,4'-bis-bromomethyldiphenyl
3,3'-Dimethoxy-4,4'-bis-bromomethyldiphenyl 4,4'-Bis-bromomethyldiphenylmethane
3,3'-Dimethoxy-4,4'-bis-bromomethyldiphenylmethane
4,4'-Bis-bromomethyldiphenylethane
3,3'-Dimethyl-4,4'-bis-bromomethyldiphenylethane
3,3'-Dimethoxy-4,4'-bis-bromomethyldiphenylethane
4,4'-Bis-bromomethyldiphenylether
3,3'-Dimethoxy-4,4'-bis-bromomethyldiphenylether
4,4'-Bis-bromomethylstilbene
3,3'-Dimethyl-4,4'-bis-bromomethylstilbene
2-Butenylene dibromide
1,4-Dimethyl-2-butenylene dibromide
1-Methyl-2-butenylene dibromide
2-Butynylene dibromide
1-Methyl-2-butynylene dibromide
1,4-Dimethyl-2-butynylene dibromide
2,4-Hexadienylene dichloride
2,4-Hexadienylene dibromide
p-Bromomethylbenzyl chloride 9. Alcohols:
$\alpha,\alpha'$-Dihydroxy-o-xylene
$\alpha,\alpha'$-Dihydroxy-m-xylene
$\alpha,\alpha'$-Dihydroxy-p-xylene
$\alpha,\alpha'$-Dihydroxy-4-methyl-m-xylene
$\alpha,\alpha'$-Dihydroxy-2,5-dimethyl-m-xylene
$\alpha,\alpha'$-Dihydroxy-4-methoxy-m-xylene
4,4'-Bis-hydroxymethyldiphenyl
4,4'-Bis-hydroxymethyldiphenylmethane
4,4'-Bis-hydroxymethyldiphenylethane
4,4'-Bis-hydroxymethylstilbene
1,4-Dihydroxy-2-butene
1,4-Dihydroxy-2-butyne
and the like dihydroxy compounds obtained by replacing halogen in the dihalides as shown in (8) above by hydroxy group 10. Ethers:
$\alpha,\alpha'$-Dimethoxy-o-xylene
$\alpha,\alpha'$-Dimethoxy-m-xylene
$\alpha,\alpha'$-Diethoxy-p-xylene
and the like ether compounds obtained by replacing halogen in the dihalides as shown in (8) above by alkyl ether group 11. Acrylonitrile
Acrylamide 12. Sulfonylating agents:
Methanesulfonyl chloride
Ethanesulfonyl chloride
Propanesulfonyl chloride
Butanesulfonyl chloride
Benzenesulfonyl chloride
p-Toluenesulfonyl chloride
m-Toluenesulfonyl chloride
o-Toluenesulfonyl chloride
p-Chlorobenzenesulfonyl chloride
m-Chlorobenzenesulfonyl chloride
o-Chlorobenzenesulfonyl chloride
p-Nitrobenzenesulfonyl chloride
m-Nitrobenzenesulfonyl chloride
o-Nitrobenzenesulfonyl chloride
p-Methoxybenzenesulfonyl chloride
m-Methoxybenzenesulfonyl chloride
o-Methoxybenzenesulfonyl chloride
and bromides thereof such as, for example,
Methanesulfonyl bromide
Ethanesulfonyl bromide
Benzenesulfonyl bromide
p-Toluenesulfonyl bromide
p-Chlorobenzenesulfonyl bromide
p-Nitrobenzenesulfonyl bromide
p-Methoxybenzenesulfonyl bromide As the dehydrohalogenating agent,
Sodium hydrogen carbonate
Potassium hydrogen carbonate
Sodium carbonate
Potassium carbonate
Sodium acetate
Potassium acetate
and
Caustic soda
may be used. Also, if circumstances permit, the basic substance used in the ring-closure, may be used.

As the solvent in the third method, aromatic hydrocarbon solvents such as benzene, xylene, etc.; halogenated aliphatic hydrocarbon solvents such as chloroform, bromoform, methylchloroform, etc.; halogenated aromatic hydrocarbon solvents such as chlorobenzene, bromobenzene, dichlorobenzenes, etc.; alcohol solvents such as methanol, ethanol, propanol, etc.; ether solvents such as diethyl ether, dimethylene glycol, dimethyl ether, diethylene glycol, etc.; sulfoxide solvents such as dimethyl sulfoxide, diethyl sulfoxide, etc.; and amide solvents such as N,N'-dimethylformamide, dimethylacetamide, N-methylpyrrolidone may be used.

Specific examples of the compounds of the general formula (I) produced by the above-mentioned methods according to the present invention which show excellent resistance to water, good fastness to light and rapid color developing speed are as follows. Shade on silica gel after development for each compound is also shown below.

| Compound | Shade after development |
|---|---|
| 2-(N-Phenylamino)-8-diethylamino benz[c]fluoran | Bluish green-black |
| 2-(N-Phenylmethanesulfonamido)-8-diethylamino-benz[c]fluoran | Dark red |
| 2-(N-Phenylamino)-8-dimethylamino-4'-nitrobenz[c]fluoran | Bluish green-black |
| 2-(N-Phenyl-benzamido)-8-dibenzyl-aminobenz[c]fluoran | Dark red |
| 2-(N-Phenylamino)-3-methoxy-8-diethylaminobenz[c]fluoran | Bluish green-black |
| 2-(N-$\alpha$-Naphthylamino)-8-diethyl-aminobenz[c]fluoran | Bluish green |
| 2-(N-$\beta$-Naphthyl-p-toluenesulfon-amido)-8-dimethylamino-benz[c]fluoran | Dark red |
| 2-(N-4-Methoxy-1-naphthylamino)-8-diethylamino-benz[c]fluoran | Bluish green-black |
| 2-(4'-Methylphenylamino)-8-dimethyl-amino-benz[c]fluoran | Green |
| 2-(4'-Methylphenylamino)-8-diethyl-amino-benz[c]fluoran | Green |
| 2-(2'-Methoxyphenylamino)-8-dimethylamino-benz[c]fluoran | Greenish black |
| 2-(2'-Methoxyphenylamino)-8-diethylamino-benz[c]fluoran | Greenish black |
| 2-(2',4'-Dimethylphenylamino)-8-dimethylamino-benz[c]fluoran | Green |
| 2-(2',4',6'-Trimethylphenylamino)-8-dimethylamino-benz[c]fluoran | Green |
| 2-(2'-Methyl-4'-chlorophenyl-amino)-8-dimethylamino-benz[c]fluoran | Green |
| 2-(2'-Methyl-4'-chlorophenyl-amino)-8-diethylamino-benz[c]fluoran | Green |
| 2-(4'-Chlorophenylamino)-8-dimethylamino-benz[c]fluoran | Green |
| 2-(4'-Chlorophenylamino)-8-diethylamino-benz[c]fluoran | Green |
| 2-(2',4',6'-Trimethylphenylamino)-8-dimethylamino-4' (or 5')-chloro-benz[c]fluoran | Green |
| 2-(2',4',6'-Trimethylphenylamino)- | Green | sorbed in the absorber. After dissolution, the mixture was warmed to 25° to 30°C for 5 hours. After cooling, the reaction mixture was then poured into 700 g of ice-water at 10° to 20°C. The mixture was neutralized with an aqueous caustic soda solution at the same temperature.

The precipitate was filtered and washed with water. The thus obtained solid 11-(2-carboxyphenyl)-2-(2',4',6'-trimethylphenylamino)-8-diethylaminobenz[c]-xanthohydrol was dissolved in 400 g of chloroform and dehydrated with 50 g of anhydrous sodium sulfate. After addition of 5 g of active charcoal, the chloroform solution was filtered while hot. The filtrate was concentrated under reduced pressure to obtain the crystals. Thus, 2-(2',4',6'-trimethylphenylamino)-8-diethylaminobenz[c]fluoran represented by the formula,

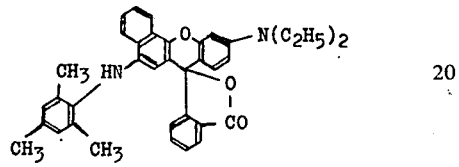

was obtained as white crystals in a yield of about 55.6 %.

Melting point: 225°- 226°C

Visible spectrum $\lambda_{max} = 441$ m$\mu$, 465.5 m$\mu$ and 630 m$\mu$ (acetic acid)

The resulting compound formed dark green color on contacting with silica gel when used as a material for pressure-sensitive copying paper. The image having excellent fastnesses to light, moisture, sublimation and alkali was produced.

EXAMPLE 2

By use of the same procedure as in Example 1, 2-(4'-methylphenylamino)-8-diethylamino-benz[c]fluoran represented by the formula,

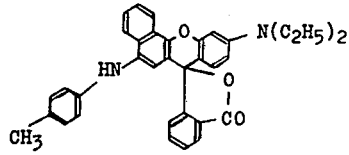

was prepared from 4-(4'-methylphenylamino)-1-naphthol and 2-(2'-hydroxy-4'-diethylaminobenzoyl)-benzoic acid.

Yield: 45.6 %. This compound formed green color on silica gel with good fastnesses to light and moisture.

EXAMPLE 3

According to the same method as in Example 1, 2-(2'-methoxyphenylamino)-8-diethylamino-benz[c]-fluoran represented by the formula,

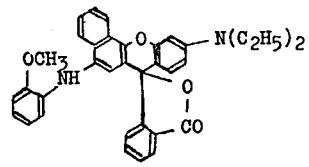

was prepared from 4-(2'-methoxyphenylamino)-1-naphthol and 2-(2'-hydroxy-4'-diethylaminobenzoyl)-benzoic acid. This derivative having a melting point of 231° to 233°C formed dark greenish black color on silica gel and had visible sepctrum $\lambda_{max} = 462.5$ m$\mu$ and 617.5 m$\mu$ (acetic acid).

EXAMPLE 4

In the same manner as in Example 1, 4-(2',4'-dimethylphenylamino)-1-naphthol and 2-(2'-hydroxy-4'-diethylaminobenzoyl)-benzoic acid was reacted to produce 2-(2',4'-dimethylphenylamino)-8-diethylamino-benz[c]-fluoran in the form of white crystals having a melting point of 147° to 148°C and a visible spectrum $\lambda_{max} = 463.0$ m$\mu$ and 620 m$\mu$ (acetic acid). This compound formed dark green color on silica gel and did not change in color during storage for a long period of time.

EXAMPLE 5

In the same manner as in Example 1, the following compounds were synthesized. Shade on silica gel is shown on the right hand column.

| Naphthylamine | Benzoyl benzoic acid | Product | Shade |
|---|---|---|---|
| (1-naphthol with 4-NH-phenyl) | (C₂H₅)₂N-phenol-CO-phenyl-COOH | (product structure) | Bluish green |
| (1-naphthol with 4-NH-(4-methylphenyl)) | (CH₃)₂N-phenol-CO-phenyl-COOH | (product structure) | Green |
| (1-naphthol with 4-NH-(2-chlorophenyl)) | (CH₃)₂N-phenol-CO-phenyl-COOH | (product structure) | Violet |

-continued

| Compound | Shade after development |
| --- | --- |
| 8-diethylamino-4' (or 5')-chloro-benz[c]fluoran | |
| 2-(N-Phenylacetylamino)-8-diethylamino-benz[c]fluoran | Red |
| 2-[N-(2',4'-Dimethylphenyl)-acetylamino]-8-diethylamino-benz[c]fluoran | Red |
| 2-[N-(2',4',6'-Trimethylphenyl)-actylamino]-8-diethylamino-benz[c]fluoran | Red |
| N-[8-Aminobenz[c]fluoran-2-yl]-N-[6-aminofluoran-2-yl]amine | Purplish blue-black |
| N-[8-Methylaminobenz[c]fluoran-2-yl]-N-[6-methylamino-fluoran-2-yl]methylamine | Purplish blue-black |
| N-[8-Dimethylaminobenz[c]fluoran-2-yl]-N-[3-methoxy-6-dimethyl-amino-fluoran-2-yl]benzylamine | Purplish blue-black |
| N-[8-Dimethylaminobenz[c]fluoran-2-yl]-N-[6-dimethylamino-fluoran-2-yl]acetamide | Dark purplish blue |
| N-[8-Dimethylamino-3'-nitrobenz[c]fluoran-2-yl]-N-[6-dimethyl-amino-3'-nitrofluoran-2-yl]-benzenesulfonamide | Dark purplish blue |
| 2-(N-β-Naphthylamino)-3',6'-dichloro-8-dimethylamino-benz[c]fluoran | Green |

As used in mark-forming systems, marking in desired areas on support webs or sheets may be accomplished by effecting localized reactive contact between the chromogenic material and the acidic material on or in such web or sheet, such chromogenic material being brought thereto by transfer, or already present therein, the reactive contact forming a clear coloration in the intended image-marking areas.

There have already been known several types of recording system utilizing an electron donor-acceptor color-forming reaction between chromogenic material and acidic material.

The pressure-sensitive recording systems generally comprise color-forming components on and/or within one or more sheet supports, the color-forming components being isolated from one another by a press-urerupturable barrier. Where the color-forming components are disposed on separate sheets as disclosed in U.S. Pat. No. 2,712,507, the record material referred to as a "transfer" or "couplet" system. In such system, a solution of a chromogenic material is held in rupturable microscopic capsules coated onto one surface of a transfer sheet, while an adjacent receiving sheet is sensitized with an acidic material, i.e. an electron acceptor. Most common acidic materials are activated acid clay and acid clays, such as attapulgite, zeolite, bentonite, kaolin and silica. Recently, monomeric phenols or acid reactant polymeric materials, such as phenolic polymers, phenyl-acetylene polymers, maleic acid-rosin resins, have been suggested either alone or in combination with acid clays.

In the manufacturing method of such record material, for instance, a non-volatile oil containing a chromogenic material dissolved therein is protected by encapsulation with coacervate film of a water-soluble polymer. The resulting coating composition containing dispersed capsules are coated on one side of a sheet, and coating composition of said electron acceptors is coated on the other side of the sheet. When several sheets are load one over another and impressed with a pencil or the like, capsules are collapsed to release the oil containing chromogenic material which produces a duplicated image on contact with the electron-acceptor. In another system as disclosed in U.S. Pat. No. 2,730,457, a coating liquid containing both of the capsules chromogenic material and acidic material is applied on one side of a sheet or alternatively, a coating containing capsules is first applied on one side of a sheet and the second coating containing the electron-acceptor is applied thereon. Thus, all the components are disposed on a single sheet, the record material is referred to as "self-contained" system and develops image color when the pressure is applied.

As a modification of pressure-sensitive marking system, Japanese Patent No. 511,757 (corresponds to U.S. Pat. Application Ser. No. 392,404, filed on Aug. 27, 1964) discloses a recording sheet, in which minute capsules containing liquid solvent are coated on one surface of a sheet support and both of the chromogenic material and the acidic polymer are coated on or impregnated in same sheet or other sheet in solid condition.

There is thermo-responsive record sheet as a mark-forming system utilizing an electron donor-acceptor color-forming reaction. For example, Japanese Patent No. 45-14039 (corresponds to U.S. Pat. Application Ser. No. 554,565 filed on June 1, 1966) discloses a temperature-responsive record material comprising a supporting sheet material having crystal violet lactone and a phenolic material solid at room temperature but capable of liquefying and/or vaporizing at normal thermographic temperatures; said lactone and phenolic material being further capable of producing a mark-forming reaction upon reactive contact.

The novel compounds of our invention are widely used for the above-mentioned mark-forming systems as a colorless chromogenic compound, i.e. electron donor and gives many excellent advantages.

According to the present invention, the above-mentioned known techniques for the production of the recording sheet are utilized using the above-mentioned fluoran compounds as a coloring material alone or in admixture with various known coloring materials to obtain the recording sheet which can form red, green or black color.

Also, it is effective for improving the color forming property and fastnesses to light and moisture of developed images to use a metal or metallic compound together with the electron-acceptor.

Thus, metals or metallic compounds such as manganese, nickel, cobalt, iron, zinc, copper, cadmium, mercury, silver, platinum, etc. are effective. Specific examples of the metallic compounds include salts and acid salts such as copper sulfate, ferrous sulfate, manganese sulfate, cobalt sulfate, zinc sulfate, nickel acetate, etc.; basic salts such as cadmium hydroxide; and oxides such as zinc oxide. They show particularly good results.

The present invention will be further specifically explained below referring to the following examples which do, of course, not limit the scope of the present invention.

EXAMPLE 1

140 Grams of 95 % sulfuric acid was charged into a four-necked flask provided with a stirrer, a thermometer and a hydrogen chloride gas absorber. A mixture of 28.0 g of 4-(2',4',6'-trimethylphenylamino)1-naphthol and 31.3 g of o-(2'-hydroxy-4'-diethylaminobenzoyl)-benzoic acid was added for one hour below 25°C. At that time, the hydrogen chloride gas evolved was ab-

EXAMPLE 6

8.12 Grams of 2-phenylamino-8-diethylaminobenz[c]fluoran and 21.4 g of benzyl bromide were maintained in 50 g of N,N-dimethylformamide at 70° to 80°C in the presence of sodium carbonate for 3 hours. The reaction mixture was then poured into ice-water to form precipitate, which was filtered and extracted with chloroform. The chloroform solution was washed with aqueous sodium carbonate and then with water several times and dried over anhydrous sodium sulfate. The extract was concentrated to obtain a syrupy product which was then filtered.

Thus, 2-(N-phenyl-N-benzylamino)-8-diethylaminobenz[c]fluoran represented by the formula,

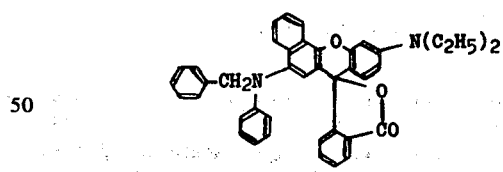

was obtained as white crystals. Yield: 80 %. The product was recrystallized from a benzene-cyclohexane mixture. This compound formed red color on silica gel.

EXAMPLE 7

In the same manner as in Example 6, the compounds of the following formulas were obtained. Shade on silica gel is shown in the right hand column.

—Continued

| Fluoran compound | | Product | Shade |
|---|---|---|---|
| [structure] | CH≡CHCH₂Br | [structure] | Dark red |
| [structure] | [PhCH₂Br] | [structure] | Dark purplish red |
| [structure] | CH₃-C₆H₄-SO₂Cl | [structure] | Dark red |
| [structure] | (PhCO)₂O | [structure] | Dark red |
| [structure] | PhCH₂Br | [structure] | Red violet |
| [structure] | CH₂=CH-CH₂Br | [structure] | Red violet |

EXAMPLE 8

10 Grams of 2-(4'-chlorophenylamino)-8-diethylamino-benz[c]fluoran was heated at about 140°C for 3 hours together with 30 g of acetic anhydride. After the reaction was completed, the unreacted acetic anhydride was removed by steam distillation to form a solid which was filtered. The solid was then recrystallized from chloroform. Thus, 2-[N-(4'-chlorophenyl)-acetylamino]-8-diethylamino-benz[c]fluoran represented by the formula,

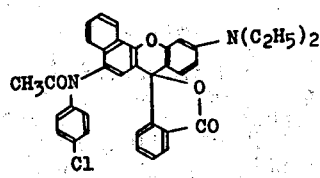

was obtained in a yield of 56.0 %. This compound formed red color on silica gel.

EXAMPLE 9

In the same manner as in Example 8, the compounds of the following formulas were obtained. Shade on silica gel is shown in the right hand column.

| Fluoran compound | | Product | Shade |
|---|---|---|---|
| [structure] | (CH₃CO)₂O | [structure] | Dark red |

The procedures of the preparation of recording sheets are illustrated by the following examples.

EXAMPLE A

In 200 g of dichlorodiphenyl was dissolved 6 g of 2-(2′,4′,6′-trimethylphenylamino)-8-diethylaminobenz[c]fluoran represented by the formula,

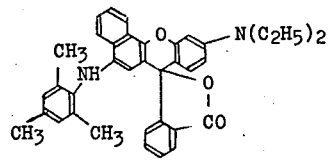

The resulting solution was mixed vigorously at 40°C with 360 g of a 11.0 % aqueous gelatin solution to make an emulsion. To the resulting emulsion, 300 g of a 10 % aqueous gum arabic solution was added. Acetic acid was added to the mixture at 40°C with stirring to adjust the pH value to 5, and water was then added to effect the coacervation of the system, whereby oil droplets containing the above-mentioned benz[c]fluoran compound were coated by the coacervated liquid wall of a complex of gum arabic and gelatin. At 5°C, the pH value of the system was further reduced to 4.4 and 5 g of 35 % formalin was added to harden the wall. In order to complete microencapsulation, 10 % sodium hydroxide was added to increase the pH value to 9 and the whole system was then gradually warmed to 50°C. The coating composition containing the thus prepared microcapsules was applied onto paper in a conventional manner. This paper was faced to the second paper onto which active clay or a phenylphenol-formaldehyde resin had been applied together with a binder. A dark green image was instantly formed on the second paper by applying pressure by means of a pencil. The thus obtained green image did not change in color and showed good fastnesses to light, water and heat.

EXAMPLE B

According to a procedure similar to that of Example A, similar pressure-sensitive copying paper was prepared from 6 g of 2-(N-phenyl-p-toluenesulfonylamino)-8-diethylamino-benz[c]fluoran represented by the formula,

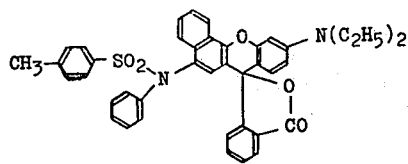

Red image was obtained by the application of pressure by handwriting. The thus obtained red color had good fastnesses to light, water and heat.

EXAMPLE C

By the same procedure as in Example A, similar pressure-sensitive copying paper was obtained from the following color precursors. The properties and fastnesses of the pressure-sensitive copying paper were the same as in Example A:

| Compound | Shade |
|---|---|
| (structure with $CH_3SO_2N$, $N(C_2H_4Cl)_2$) | Red |
| (structure with NH-naphthyl, $N(CH_2CH_3)_2$) | Green |
| (structure with NH-phenyl, $N(C_2H_5)_2$) | Bluish green-black |
| (structure with $C_6H_5CH_2$-N, $N(C_2H_5)_2$) | Dark red |
| (structure with $CH_3$, NH, $N(C_2H_5)_2$) | Green |
| (structure with $CH_3O$, NH, $N(C_2H_5)_2$, $NO_2$) | Greenish black |
| (structure with NH, $N(CH_3)_2$, $NO_2$) | Bluish green-black |
| (structure with $CH_2CO$-N, $CH_3$, $N(CH_2CH_2OCH_3)_2$) | Dark red |
| (structure with $CH_3CH=CHCH_2$-N-naphthyl, $N(C_2H_5)_2$) | Dark purplish red |

| Compound | Shade |
|---|---|
| [structure] | Bluish green-black |
| [structure] | Bluish green-black |
| [structure] | Dark red |
| [structure] | Dark red |
| [structure] | Bluish green-black |

EXAMPLE D

In the same manner as in Example A, pressure-sensitive copying paper was prepared using 2-(2',4'-dimethylphenylamino)-8-dimethylamino-benz[c]fluoran as an electron donating color former and activated clay as an electron-acceptor. Copied image obtained on the electron acceptor-coated surface was dark green in color and showed excellent fastnesses to light and moisture like that of Example A.

EXAMPLE E

Pressure-sensitive copying paper was prepared in the same manner as in Example A except that 3 parts by weight of 2-(2',4',6'-trimethylphenylamino)-8-diethylamino-benz[c]fluoran and 3 parts of 2-dimethylamino-8-dipropylamino-benz[c]fluoran, which may form dark reddish violet color, as electron donating color formers were dissolved in 100 parts by weight of trichlorodiphenyl. Copied image obtained on the electron-acceptor surface was black in color and maintained the original color during storage for a long period of time.

EXAMPLE F

Pressure-sensitive copying paper which may form black color images was obtained in the same manner as in Example E except that 3 parts by weight of 2-[N-(2',4'-dimethoxyphenyl)-amino]-8-methylamino-benz[c]-fluoran and 3 parts by weight of 2-methyl-6-diethylaminofluoran were used as electron donating color formers.

EXAMPLE G

In 100 parts by weight of trichlorodiphenyl, 4 parts by weight of 2-(2'-methyl-4'-methoxyphenylamino)-8-diethylamino-benz[c]fluoran was dissolved at 100°C. The color former-containing oil was dispersed in a mixture of 500 parts by weight of a 10 % gelatin solution and 500 parts by weight of a 10 % gum arabic solution at 60°C to form an emulsion. Then, 1,000 parts by weight of warm water at 40°C was added to dilute the emulsion.

A 10 % acetic acid solution was gradually added dropwise at 50°C with stirring to adjust the pH value to 4 – 4.3. The emulsion was cooled to a temperature below 15°C. At this temperature, 500 parts by weight of a 20 % dispersion of titanium oxide having a particle size of 0.2 to 0.4 $\mu$ was added and 100 parts by weight of a 10 % formalin was then added. Further, 10 % caustic soda was gradually added dropwise to adjust the pH value to 10 – 10.5. The thus obtained dispersion is referred to as "A liquid".

On the other hand, 40 parts by weight of 10 % caustic soda and 200 parts by weight of activated clay were dispersed in 400 parts by weight of water. Then, 200 parts by weight of a 10 % polyvinyl alcohol was added. The thus obtained dispersion was uniformly mixed with the above-mentioned A liquid to obtain a coating composition.

The coating composition was applied onto one side of 40 g/m² paper in an amount of 7 g/cm² on dry basis and then dried. The resulting pressure-sensitive copying paper is a "self-contained" type. When pressure was applied onto the coated surface, blackish green color was formed which did neither change nor disappear on exposure to light or moisture.

EXAMPLE H

The capsule-containing coating liquid as prepared in Example G was applied onto one side of 45 g/m² paper in an amount of 5 g/m² on dry basis and dried. Further, the electron-acceptor containing coating liquid as prepared in Example A was applied onto the coated surface in an amount of 4 g/m² and dried. The resulting pressuresensitive copying paper is a "self-contained" type containing both a color former capsule-coated layer and an electron-acceptor-coated layer on one side of the paper.

Good pressure-sensitive copying paper can be prepared by replacing the electron-acceptor-containing coating liquid used in the above-mentioned examples by coating liquids of the following recipes:

| | | Parts by weight |
|---|---|---|
| (a) | Water | 100 |
| | Acid clay | 100 |
| | Cadmium hydroxide | 10 |
| | Styrene-butadiene latex | 20 |
| (b) | Water | 200 |
| | Acid clay | 100 |
| | Manganese sulfate | 5 |
| | Styrene-butadiene latex | 15 |
| (c) | Water | 200 |
| | Acid clay | 100 |
| | Copper sulfate | 3 |
| | Latex | 10 |
| (d) | Water | 200 |
| | Acid clay | 100 |
| | Ferrous sulfate | 3 |
| | Latex | 15 |

-continued

| | | Parts by weight |
|---|---|---|
| (e) | Water | 200 |
| | Acid clay | 100 |
| | Zinc acetate | 10 |
| | Latex | 20 |
| (f) | Water | 200 |
| | Acid clay | 100 |
| | Cobalt sulfate | 5 |
| | Latex | 15 |
| (g) | Water | 200 |
| | Acid clay | 100 |
| | Nickel sulfate | 5 |
| | Latex | 15 |
| (h) | Water | 200 |
| | Attapulgite | 100 |
| | Zinc oxide | 5 |
| | Latex | 15 |

EXAMPLE I

In 100 parts by weight of trichlorodiphenyl, 4 parts by weight of 2-(2',4'-dimethylphenylamino)-8-ethylamino-benz[c]fluoran was dissolved at 100°C. The color former-containing oil was dispersed in 500 parts by weight of a 7 % gelatin solution at 60°C to form an emulsion. To the emulsion, 350 parts by weight of a 10 % gum arabic solution was added and 550 parts by weight of warm water was added. A 10 % acetic acid solution was gradually added dropwise at 50°C with stirring to adjust the pH value to 4.0 – 4.3 and the emulsion was cooled to a temperature below 10°C. 200 Parts by weight of a 50 % dispersion of titanium oxide having a particle size of 0.2 to 0.5 μ was gradually added at this temperature with stirring. 38 Parts by weight of 37 % formalin was then added and a 10 % caustic soda solution was added dropwise to adjust the pH value to 10.0 to 10.5. The thus obtained dispersion is referred to as "A liquid".

On the other hand, 20 parts by weight of zinc oxide and 40 parts by weight of a 28 % ammonia water was added to 400 parts by weight of water. Then, 200 parts by weight of acid clay was dispersed in the mixture and one part by weight of sodium alginate was added. Further, 100 parts by weight of a 10 % polyvinyl alcohol solution was added and the whole was well mixed. The resulting dispersion was mixed with the above-mentioned A liquid and 250 parts by weight of a 10 % polyvinyl alcohol solution and 100 parts by weight of pulp powder to form a coating composition.

This coating composition was applied onto one side of 40 g/m² paper in an amount of 10 g/m² on dry basis and dried. The thus obtained pressure-sensitive copying paper is so-called "self-contained" type copying paper. Dark green image could be instantly formed by the application of pressure and the obtained image did neither change in color nor disappear on exposure to light or moisture.

EXAMPLE J

Similar pressure-sensitive copying paper could be prepared by replacing 2-(2',4'-dimethylphenylamino)-8-diethylamino-benz[c]fluoran used in Example I by the following fluoran compounds. Shade of the image obtained is shown in the right hand column.

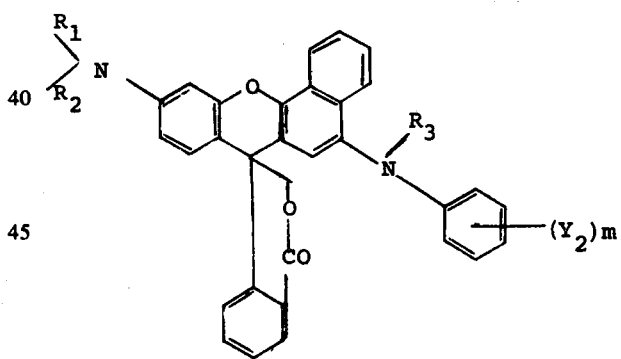

EXAMPLE K

A thermo-responsive (or heat-sensitive) recording material is manufactured by the following manner. 20 Parts by weight of 2-(2',4'-dimethoxyphenylamino)-6-diethylamino-benz[c]fluoran, 15 parts by weight of 3-diethylamino-6-methylfluoran, 150 parts by weight of a 10 % aqueous solution of polyvinyl alcohol, and 65 parts by weight of water were dispersed in a high shear mixer. (Component A). 35 Parts by weight of Bisphenol A, 150 parts by weight of the polyvinyl alcohol solution, and 65 parts by weight of water were dispersed in a high shear mixer. (Component B). 3 Parts by weight of Component A and 67 parts by weight of Component B were combined and coated on the paper sheet at a dry weight of 5 g/m². The resulting sheet may be used alone as a copy-receiving sheet by being served with a pattern of heat from front or back, as by a thermographically-heated original document, by trace of hot stylus, by hot type, or by any other means giving a heat pattern by conduction. Developed image of this sheet is clear black.

What is claimed is:

1. A compound represented by the formula:

[Structural formula with $R_1$, $R_2$, $R_3$, $(Y_2)_m$]

wherein $R_1$ and $R_2$ each signify a lower alkyl group, $R_3$ signifies hydrogen, $Y_2$ signifies hydrogen, a lower alkyl or lower alkoxy group, and $m$ is an integer of 1 to 3.

2. A compound represented by the formula,

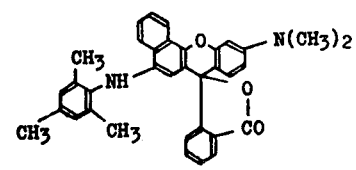

3. A compound represented by the formula,

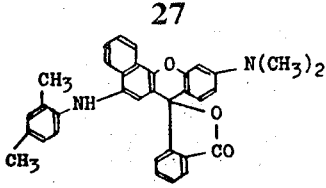
4. A compound represented by the formula,
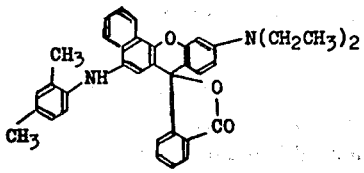
5. A compound represented by the formula,
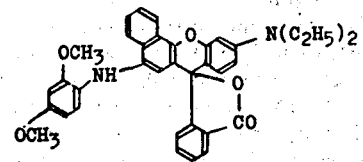
6. A compound represented by the formula,
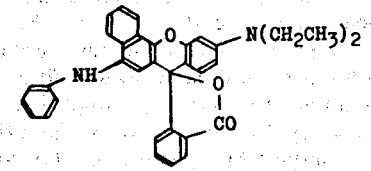
7. A compound represented by the formula,
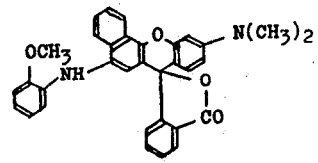
8. A compound represented by the formyla,
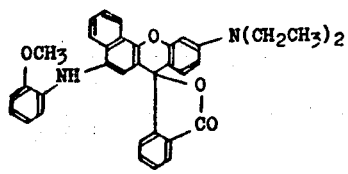
9. A compound represented by the formula,
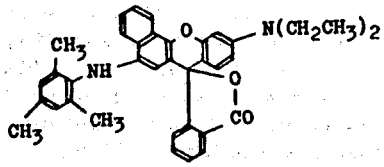
* * * * *